US008597221B2

(12) United States Patent
Lisowski

(10) Patent No.: US 8,597,221 B2

(45) Date of Patent: Dec. 3, 2013

(54) TRACTION EXERCISE APPARATUS

(76) Inventor: Andrew Lisowski, Los Angles, CA (US)

( * ) Notice: Subject to any disclaimer, the term of this patent is extended or adjusted under 35 U.S.C. 154(b) by 717 days.

(21) Appl. No.: 12/729,016

(22) Filed: Mar. 22, 2010

(65) Prior Publication Data

US 2011/0230808 A1 Sep. 22, 2011

(51) Int. Cl.

| | |
|---|---|
| ***A61F 5/00*** | (2006.01) |
| ***A63B 21/002*** | (2006.01) |
| ***A63B 21/068*** | (2006.01) |
| ***A63B 21/04*** | (2006.01) |
| ***A63B 21/00*** | (2006.01) |
| ***A63B 71/00*** | (2006.01) |
| ***A63B 26/00*** | (2006.01) |
| ***A63B 7/02*** | (2006.01) |
| ***A63B 9/00*** | (2006.01) |
| ***A63B 17/00*** | (2006.01) |
| ***A63B 1/00*** | (2006.01) |
| ***A63B 23/00*** | (2006.01) |
| ***A47D 13/04*** | (2006.01) |
| ***A61G 5/00*** | (2006.01) |

(52) U.S. Cl.

USPC .................. 602/36; 602/32; 602/33; 602/34; 602/35; 482/91; 482/130; 482/131; 482/133; 482/134; 482/139; 482/907; 482/23; 482/24; 482/35; 482/36; 482/37; 482/38; 482/43; 482/69; 482/143; 482/144; 482/145; 482/148; 482/96; 606/241; 5/81.1 R; 5/83.1; 5/84.1; 5/87.1

(58) Field of Classification Search

USPC ............... 602/32–36; 601/24, 26, 33; 482/91, 482/130, 131, 133, 134, 139, 907, 23, 24, 482/35–38, 43, 69, 143, 144, 145, 148, 96; 272/144, 145, 93, 62, 63; 606/241; 5/81 R, 83.1, 84.1, 87.1

See application file for complete search history.

(56) References Cited

U.S. PATENT DOCUMENTS

| | | | | |
|---|---|---|---|---|
| 5,472,414 | A * | 12/1995 | Detty | 602/27 |
| 6,241,644 | B1 * | 6/2001 | Tepperberg | 482/121 |
| 7,303,517 | B2 * | 12/2007 | Pandozy | 482/144 |

* cited by examiner

*Primary Examiner* — Patricia Bianco
*Assistant Examiner* — Nihir Patel
(74) *Attorney, Agent, or Firm* — John Alumit

(57) ABSTRACT

A traction exercise apparatus comprises a rectangular shaped metal frame including a pair of metal vertical members, a metal horizontal member on a bottom side, and a pair of metal horizontal members on a top side. A first rotating metal shaft and a second rotating metal shaft are located across the pair of metal horizontal members. Further a pair of ankle braces is attached to a snap hook. A cable pulley on each side of the first rotating metal shaft supports a first metal cable attached to the snap hook. A first cable reel on each side of second rotating metal shaft supports the first metal cable. A second cable reel on each side of the second rotating metal shaft supports a second metal cable attached to a hand grab bar. Second rotating metal shaft rotates to transmit a tension to the first metal cable to perform different traction exercises.

16 Claims, 8 Drawing Sheets

SECT A-A

TRACTION EXERCISE APPARATUS

CROSS-REFERENCE TO RELATED APPLICATION

Not Applicable

FEDERALLY SPONSORED RESEARCH

Not Applicable

SEQUENCE LISTING OR PROGRAM

Not Applicable

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND

The invention relates to a traction exercise apparatus, and more particularly to a traction exercise apparatus that provides traction force to various body parts as desired.

Traction is a pulling force that elongates or stretches the spine. This pulling force is used for the treatment of musculoskeletal conditions. The traction force may be applied to the arms, legs, neck, back or pelvis for treatment of fractures, dislocations, muscle spasms and other muscular disorders. There are different traction devices available today that can be used at home. For example, traditional traction devices used in a sitting position and more advanced traction devices used in a lying down position. The advanced devices use weights, counterweights and pulleys to provide a force that gradually stretches the spine to a normal position.

There are well-known traction exercise machines that uses a spring to provide resistive force to the joints. One such device is described in U.S. Patent Application No. 20090299248 to Cha (Dec. 3, 2009). This device includes a traction spring, a belt, and a traction control unit. The traction control unit interconnects the spring and the belt, and includes a locking mechanism. The belt is connected to the ankles of the user. The traction spring is arranged to be hooked onto a door frame.

A number of other exercise devices are known in the art for stretching and strengthening the muscles of the lower back and legs of the user. An example of such devices includes U.S. Pat. No. 5,261,865 issued to Trainor (Nov. 16, 1993). The device comprises a backboard for supporting the user's back and pelvis and a belt to restrain the user's pelvis. A single cable is provided with sliding handles, a pulley guiding system, and leg supporting slings. In a stretching exercise mode, the handles are slowly pulled by the user to raise the legs and thereby stretching the supporting muscles of the spine. In a strengthening exercise mode, the user's feet are pushed toward the floor against the resistance provided by the muscles of the arms.

Another prior art, U.S. Pat. No. 4,489,713 issued to Latenser (Dec. 25, 1984), describes a traction invention with a bed and an overhead traction frame, from which a gear motor is suspended to adjust the vertical position of a knee and ankle supporting mechanism. The knee and ankle supporting mechanism comprises a transversely extending knee support adapted to fit beneath the user's knees. An elongated member is secured to the knee support and extends therefrom towards the user's feet. A transversely extending ankle support is secured to the end of the elongated member and is adapted to be positioned over the user's ankles.

Finally, U.S. Pat. No. 7,303,517 issued to Pandozy (Dec. 4, 2007) describes an inversion apparatus for performing exercises of suspending the body of a person in an inverted position, including a stable steel frame, a winch and a pair of padded anchor rings that connect the feet of the person to a winch operated by a motor or manually. Horizontal cross bars are present on the steel frame to assist the user in performing exercises while suspended in the inversion apparatus.

Most of the above traction exercise devices have considerable drawbacks. Spring utilizing devices provide traction force only to the legs. Moreover, injury can easily occur if the belt is released before the tension within the spring returns to a relaxed state, or if the device for holding the legs is too loose so that the legs slip out during suspension. Further, such stretching devices have been known for stretching the inside thigh muscles and the lower back muscles of a user, but are incapable of stretching the other joints and muscle groups of the human body. Moreover, the above-explained systems are relatively complex and time-consuming to set up.

It is therefore, an object of the present invention to provide a traction exercise device which is easily set up, simple in application, safe to use, and provides traction force to various body parts including the ankles, leg, neck, wrist and hip joint.

SUMMARY

The present invention discloses a traction exercise apparatus. The apparatus comprises a rectangular shaped metal frame including a pair of metal vertical members on each of a right side and a left side thereof, a metal horizontal member having a planar surface on a bottom side thereof, and a pair of metal horizontal members on a top side thereof. A metal cross member is fixed proximate to each of a right edge and a left edge of the pair of metal horizontal members. A first metal shaft, rotating or fixed, and a second metal shaft, rotating or fixed, located across the pair of metal horizontal members and proximate to each of the metal cross member.

A pair of ankle braces is included that is being adapted to be worn on the feet of a user. The pair of ankle braces includes a fabric covering, a plurality of fabric straps encircling the fabric covering, and a pair of elongated fabric straps extending on an outer side of the fabric covering. The pair of elongated fabric straps has a proximal end sewn to the fabric covering and a distal end attached to a snap hook.

Further, the traction exercise apparatus comprises a cable pulley supporting a first metal cable attached to the snap hook wherein the cable pulley being on each side of the first rotating or fixed metal shaft, and a first cable reel supporting the first metal cable on each side of the second rotating or fixed metal shaft. A second cable reel supporting a second metal cable is attached to a hand grab bar wherein the second cable reel being on each side of the second rotating or fixed metal shaft.

The user can lift himself/herself using the hand grab bar after securely supporting the ankles of the user by the first metal cable. In use, the hand grab bar applies a tension to the second metal cable to cause the rotation of the second rotating metal shaft thereby transmitting the tension to the first metal cable to perform a plurality of different traction exercises.

Although particular embodiments of the present invention have been described in the foregoing description, it is to be understood that the present invention is not to be limited to just the embodiments disclosed, but that they are capable of numerous rearrangements, modifications and substitutions without departing from the description herein.

REFERENCE NUMERALS

Figure 1:
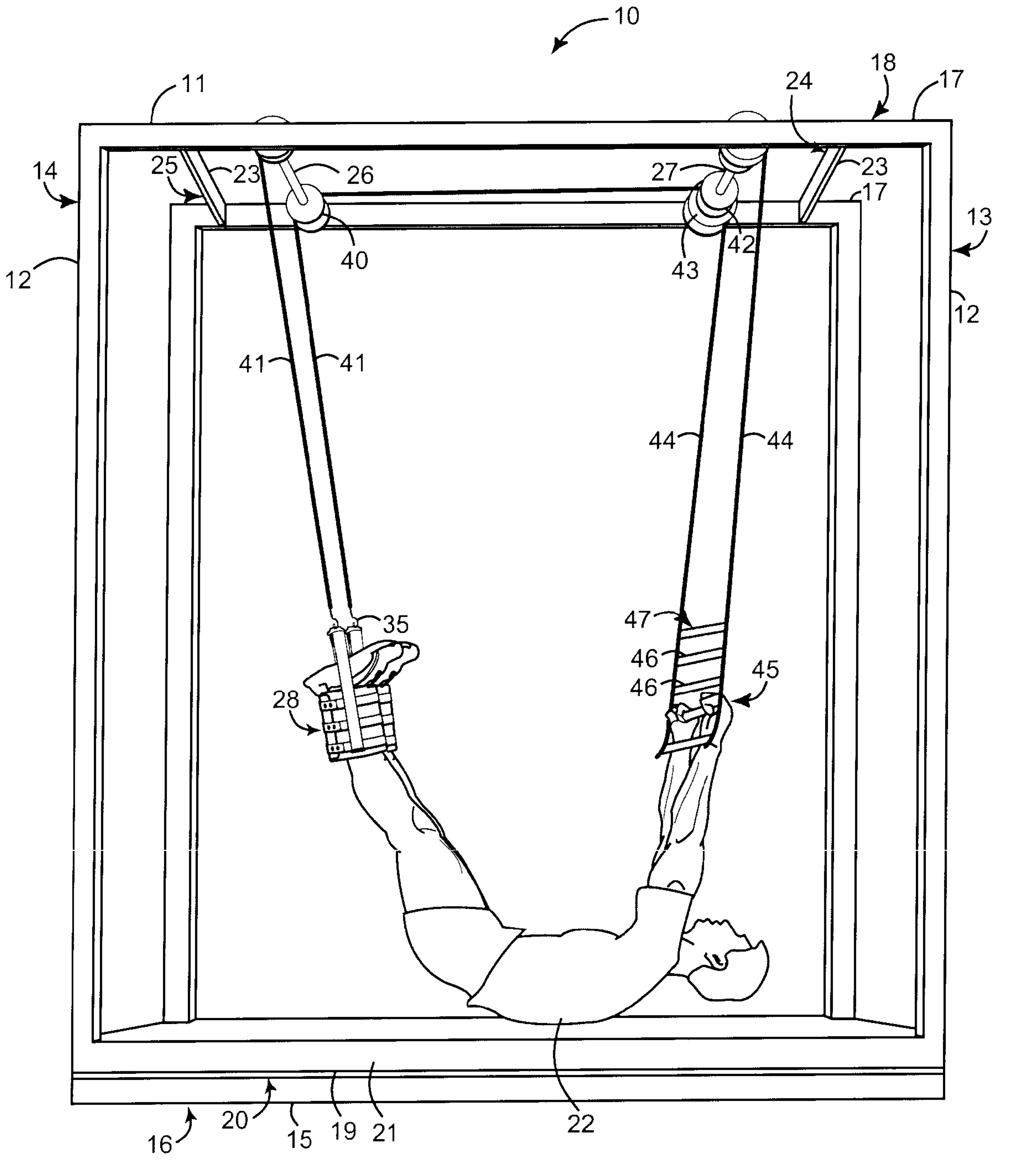
FIG. 1 is a perspective side view of a traction exercise apparatus showing a user in an initial position according to the present invention.

10 . . . A traction exercise apparatus
11 . . . A rectangular shaped metal frame
12 . . . A pair of metal vertical members
13 . . . A right side of the rectangular shaped metal frame
14 . . . A left side of the rectangular shaped metal frame
15 . . . A metal horizontal member having a planar surface
16 . . . A bottom side of the rectangular shaped metal frame
17 . . . A pair of metal horizontal members
18 . . . A top side of the rectangular shaped metal frame
19 . . . A table
20 . . . A top side of the metal horizontal member having a planar surface
21 . . . A mat
22 . . . A user
23 . . . A metal cross member
24 . . . A right edge of the pair of metal horizontal members
25 . . . A left edge of the pair of metal horizontal members
26 . . . A first rotating or fixed metal shaft
27 . . . A second rotating or fixed metal shaft
28 . . . A pair of ankle braces
29 . . . A fabric covering
30 . . . A plurality of fabric straps
31 . . . A pair of elongated fabric straps
32 . . . An outer side of the fabric covering
33 . . . A proximal end of the pair of elongated fabric straps
34 . . . A distal end the pair of elongated fabric straps
35 . . . A snap hook
36 . . . A buckle
37 . . . A plurality of metal reinforced holes
38 . . . A synthetic foam material
39 . . . An inner side of the ankle brace
40 . . . A cable pulley
41 . . . A first metal cable
42 . . . A first cable reel
43 . . . A second cable reel
44 . . . A second metal cable

45 . . . A hand grab bar
46 . . . A plurality of rungs
47 . . . A soft grip material
48*a*, 48*b*, 48*c* . . . A first pipe in 3 parts (collectively referred to as 48)
49*a*, 49*b*, 49*c* . . . A second pipe in 3 parts (collectively referred to as 49)
50 . . . A shaft support for the second rotating or fixed metal shaft
51 . . . A first cable reel pipe
52 . . . A second cable reel pipe
53 . . . A bolt
54 . . . An opening
55 . . . A Shaft Support for the first rotating or fixed metal shaft

DETAILED DESCRIPTION

Figure 2:
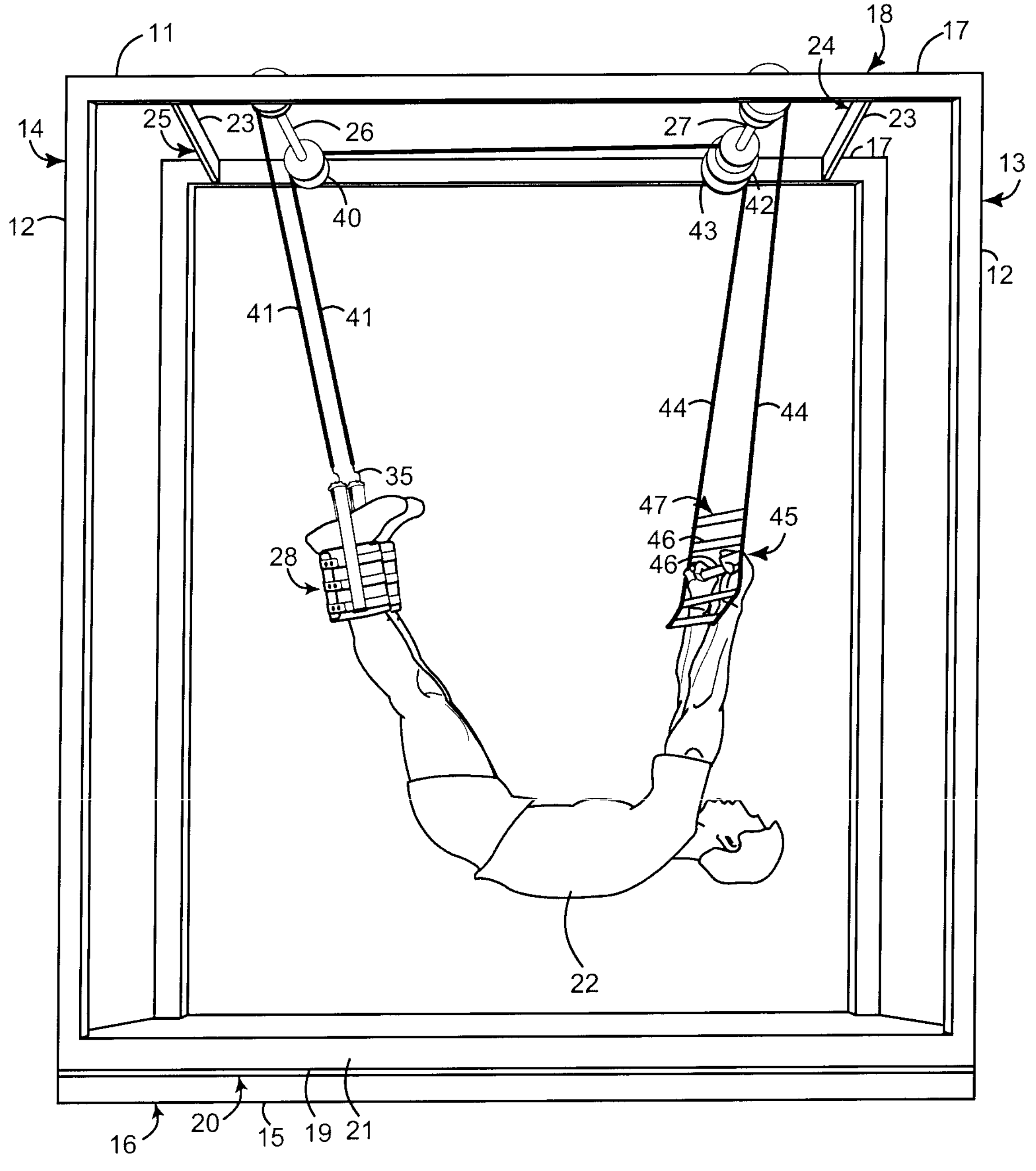
FIG. 2 is a perspective side view of the present invention showing the user in an intermediate position.
Figure 3:
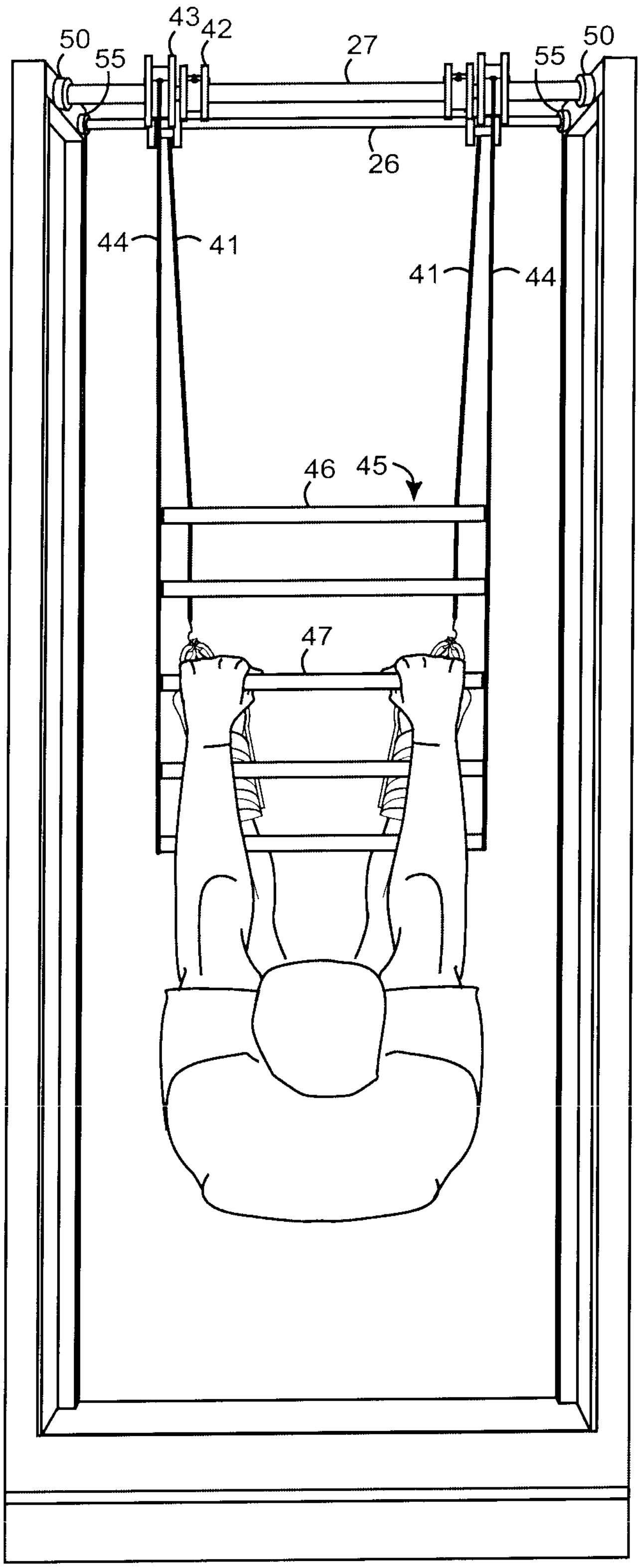
FIG. 3 is a perspective front view of the traction exercise apparatus shown in FIG. 2.

Referring to the drawings, a preferred embodiment of a traction exercise apparatus 10 is illustrated from FIGS. 1 through 10. As shown in FIGS. 1-3, the traction exercise apparatus 10 of the present invention comprises a rectangular shaped metal frame 11 including a pair of metal vertical members 12 on each of a right side 13 and a left side 14 thereof, a metal horizontal member having a planar surface 15 on a bottom side 16 thereof, and a pair of metal horizontal members 17 on a top side 18 thereof. The metal horizontal member having a planar surface 15 includes a table 19 on a top side 20 thereof and the table 19 includes a mat 21 to provide support and cushioning effect to a user 22. The pair of metal vertical members 12 supports the pair of metal horizontal members 17 and the user 22. A metal cross member 23 is fixed proximate to each of a right edge 24 and a left edge 25 of the pair of metal horizontal members 17. The metal cross member 23 provides rigidity to the rectangular shaped metal frame 11. A first rotating or fixed metal shaft 26 and a second rotating or fixed metal shaft 27 is located across the pair of metal horizontal members 17 and proximate to each of the metal cross member 23.

A pair of ankle braces (FIGS. 4-5) 28 is included that is being adapted to be worn on the feet of the user 22. The pair of ankle braces 28 includes a fabric covering 29, a plurality of fabric straps 30 encircling the fabric covering 29, and a pair of elongated fabric straps 31 extending on an outer side of the fabric covering 32. The pair of elongated fabric straps 31 has a proximal end 33 sewn to the fabric covering 29 and a distal end 34 attached to a snap hook 35.

Figure 4:
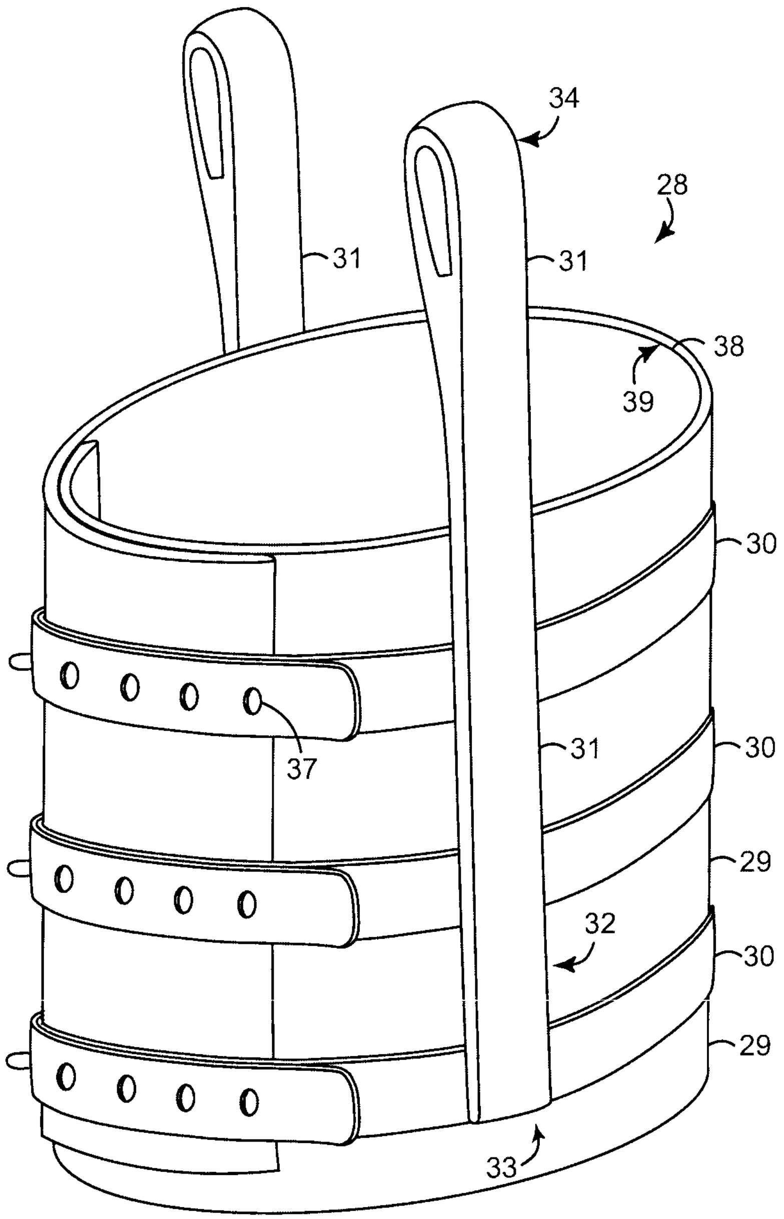
FIG. 4 is a perspective side view of an ankle brace according to the present invention.
Figure 5:
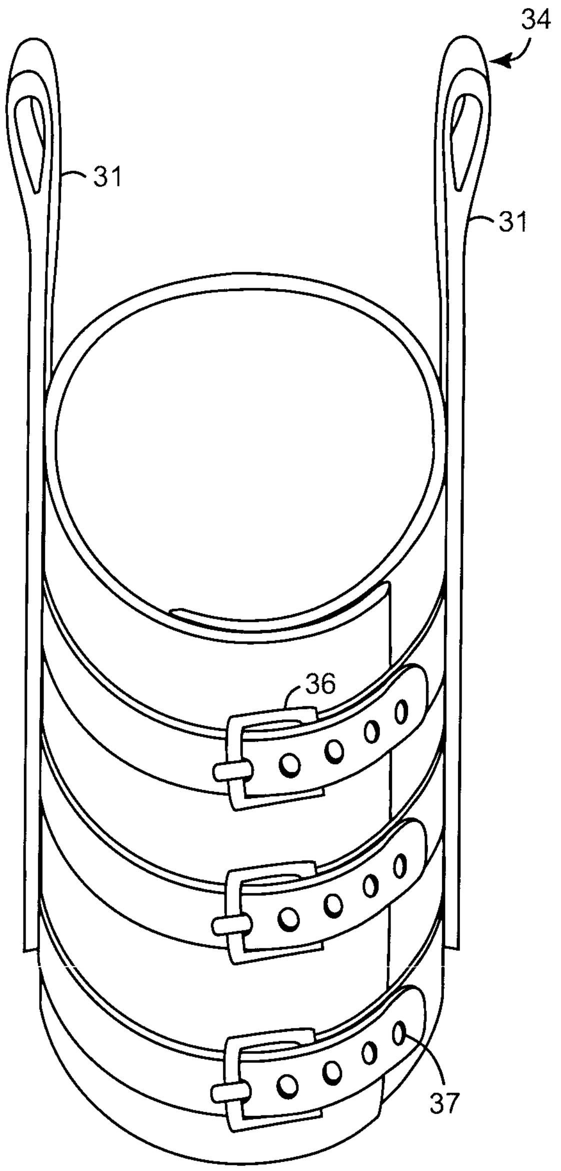
FIG. 5 is a perspective top down view of the ankle brace shown in FIG. 4.

As shown in FIGS. 4-5, each of the plurality of fabric straps 30 includes a buckle 36 to secure the pair of ankle braces 28 to the ankle of the user 22. The buckle 36 may be utilized to apply a pressure on the ankle of the user 22. The plurality of fabric straps 30 has a plurality of metal reinforced holes 37 for the buckle 36. A polyurethane foam material 38 is included on an inner side of the ankle brace 39. However, the foam can also be made of plastic or other synthetic material. The polyurethane foam material 38 distributes the pressure evenly on the ankle of the user 22. The fabric covering 29, plurality of fabric straps 30, and pair of elongated fabric straps 31 may be stitched or glued together for protection and durability.

Further, the traction exercise apparatus 10 comprises a cable pulley 40 supporting a first metal cable 41 attached to the snap hook 35 wherein the cable pulley 40 being on each side of the first rotating metal shaft 26, and a first cable reel 42 supporting the first metal cable 41 on each side of the second rotating metal shaft 27. A second cable reel 43 supporting a second metal cable 44 is attached to a hand grab bar 45 wherein the second cable reel 43 being on each side of the second rotating metal shaft 27. The user 22 can lift himself/ herself using the hand grab bar 45 after securely supporting the ankles of the user 22 by the first metal cable 41. The hand grab bar 45 may include a plurality of rungs 46 to facilitate the user 22 to move up and down. The hand grab bar 45 is covered with a soft grip material 47 and comprises material including wood, metal, and plastic. In use, the hand grab bar 45 applies a tension to the second metal cable 44 to cause the rotation of the second rotating metal shaft 27 thereby transmitting the tension to the first metal cable 41 to perform a plurality of different traction exercises. Thus the tension on the first metal cable 41 elevates the feet of the user 22.

Figure 6:
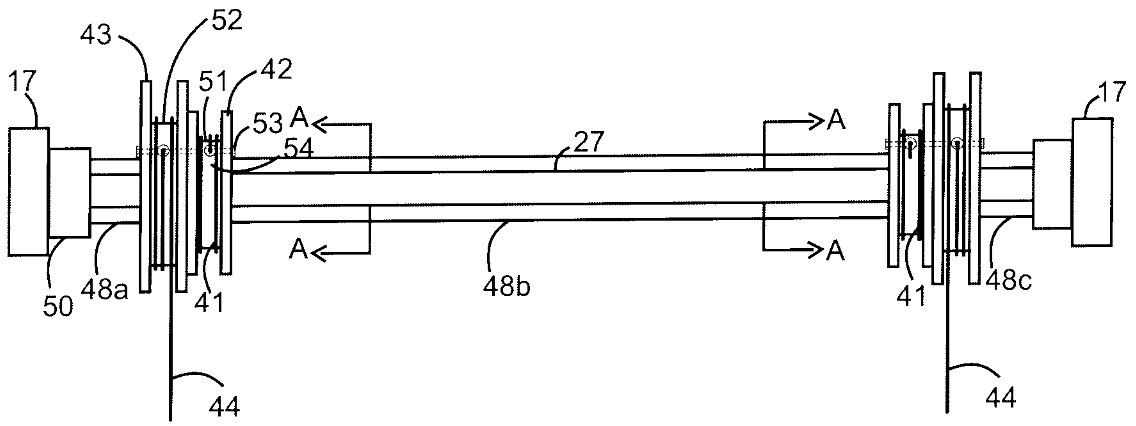
FIG. 6 is a plan view of a second rotating metal shaft.
Figure 7:
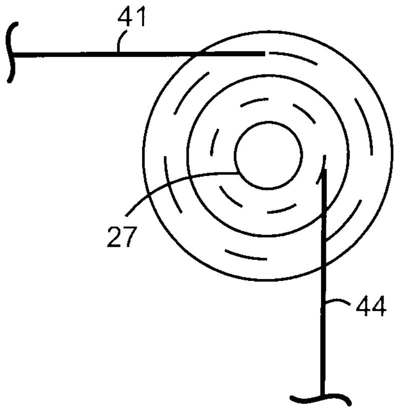
FIG. 7 is a front view of the second rotating metal shaft taken along the lines A-A of FIG. 6.

As shown in FIG. 6, a first pipe 48 secures the second cable reel 43 and prevents it from moving sideways along second rotating or fixed metal shaft 27. By tightening a screw 49 on the first pipe 48, the first cable reel 42 and the second cable reel 43 are secured to the second rotating metal shaft 27. The rotating or fixed metal shaft 27 is inserted into the first pipe 48, and the rotating or fixed metal shaft 27 is inserted into a Shaft Support 50 that is attached to the pair of metal horizontal members 17. As shown, a first cable reel pipe 51 provides support to the first metal cable 41 and a second cable reel pipe 52 provides support to the second metal cable 44. FIG. 7 is a front view of the second rotating metal shaft 27 taken along the lines A-A of FIG. 6. A bolt 53 is extending from the first cable reel 42 to the second cable reel 43 wherein the bolt 53 is being inside the reel pipes 51, 52 to provide support to the first metal cable 41 and the second metal cable 44. An opening 54 in both the reel pipes 51, 52 provides access to secure the first metal cable 41 and second metal cable 44 to the bolt 53.

Figure 8:
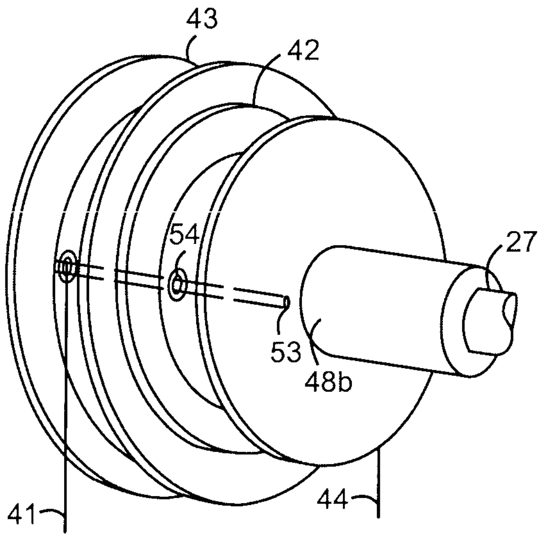
FIG. 8 is a perspective side view of a first cable reel and a second cable reel on the second rotating metal shaft.
Figure 9:
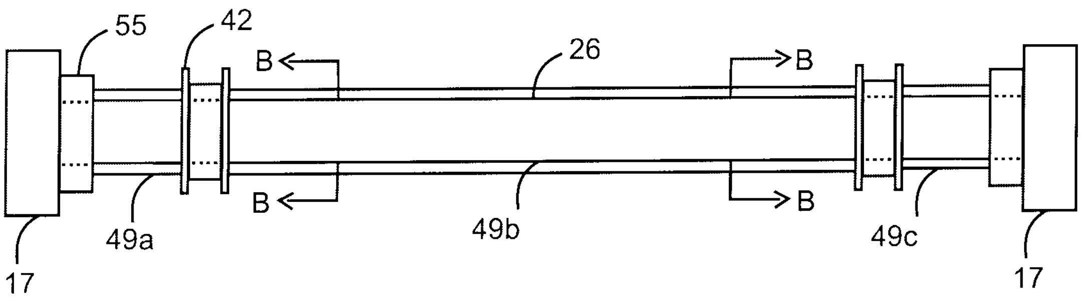
FIG. 9 is a plan view of a first rotating metal shaft.
Figure 10:
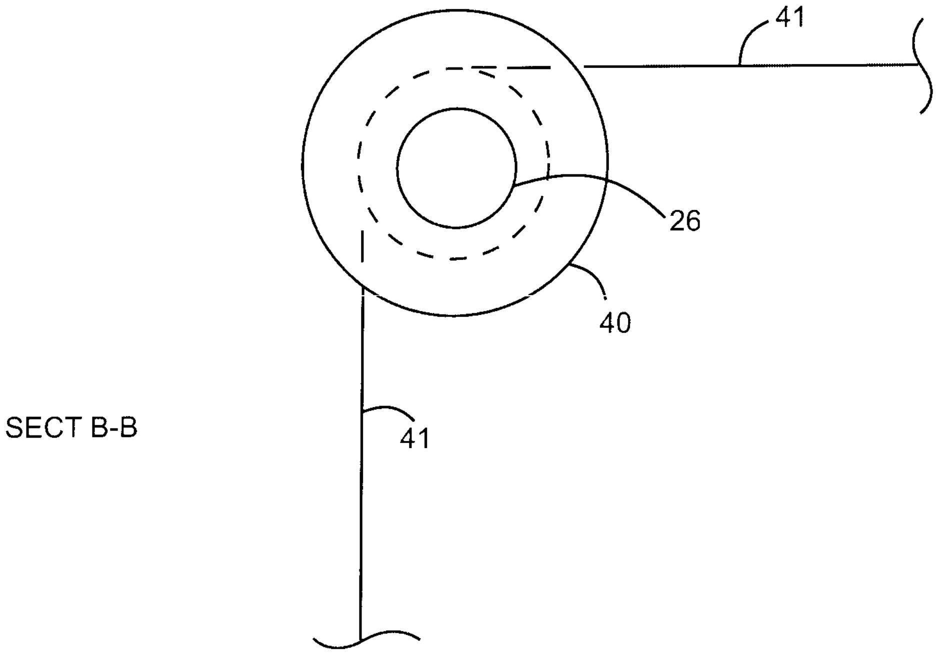
FIG. 10 is a front view of the first rotating metal shaft taken along the lines B-B of FIG. 9.

A perspective side view of the first cable reel 42 and the second cable reel 42 on the second rotating metal shaft 27 is shown in FIG. 8. Referring to FIG. 9, the first rotating metal shaft 26 is inserted to a Shaft Support 55 that is attached to the pair of metal horizontal members 17. FIG. 10 is a front view of the first rotating metal shaft 26 taken along the lines B-B of FIG. 9.

All features disclosed in this specification, including any accompanying claims, abstract, and drawings, may be replaced by alternative features serving the same, equivalent or similar purpose, unless expressly stated otherwise. Thus, unless expressly stated otherwise, each feature disclosed is one example only of a generic series of equivalent or similar features.

Although preferred embodiments of the present invention have been shown and described, various modifications and substitutions may be made thereto without departing from the spirit and scope of the invention. Accordingly, it is to be understood that the present invention has been described by way of illustration and not limitation.

What is claimed is:

1. A traction exercise apparatus, comprising a rectangular shaped metal frame including a pair of metal vertical members on each of a right side and a left side thereof, a metal horizontal member having a planar surface on a bottom side thereof, and a pair of metal horizontal members on a top side thereof;

a metal cross member proximate to each of a right edge and a left edge of the pair of metal horizontal members;

a first rotating or fixed metal shaft and a second rotating or fixed metal shaft located across the pair of metal horizontal members and proximate to each of the metal cross member;

a pair of ankle braces having a fabric covering;

a plurality of fabric straps encircling the fabric covering;

a pair of elongated fabric straps extending on an outer side of the fabric covering and having a proximal end sewn to the fabric covering and a distal end attached to a snap hook;

a cable pulley supporting a first metal cable attached to the snap hook, the cable pulley being on each side of the first rotating or fixed metal shaft;

a first cable reel supporting the first metal cable on each side of the second rotating metal shaft; and a second cable reel supporting a second metal cable attached to a hand grab bar, the second cable reel being on each side of the second rotating metal shaft;

whereby the hand grab bar applies a tension to the second metal cable to cause the rotation of the second rotating metal shaft thereby transmitting the tension to the first metal cable to perform a plurality of different traction exercises.

2. The apparatus of claim 1, wherein the tension on the first metal cable elevates the feet of a user.

3. The apparatus of claim 2, wherein the hand grab bar is made from material including wood, metal, or plastic.

4. The apparatus of claim 1, wherein the metal horizontal member includes a table on a top side thereof.

5. The apparatus of claim 4, wherein the table includes a mat to provide support and cushioning effect to the user.

6. The apparatus of claim 1, wherein the user can lift himself/herself using the hand grab bar after securely supporting the ankles of the user by the first metal cable.

7. The apparatus of claim 1, wherein the hand grab bar includes a plurality of rungs to facilitate the user to move up and down.

8. The apparatus of claim 1, wherein the hand grab bar is covered with a soft grip material.

9. The apparatus of claim 1, wherein the pair of metal vertical members supports the pair of metal horizontal members and the user.

10. The apparatus of claim 1, wherein the metal cross member provides rigidity to the rectangular shaped metal frame.

11. The apparatus of claim 1, wherein each of the plurality of fabric straps includes a buckle to secure the ankle brace to the ankle of the user.

12. The apparatus of claim 11, wherein the buckle may be utilized to apply a pressure on the ankle of the user.

13. The apparatus of claim 1, wherein the plurality of fabric straps has a plurality of metal reinforced holes for the buckle.

14. The apparatus of claim 1, wherein the ankle brace includes a synthetic foam foam material, such as polyurethane, on an inner side thereof.

15. The apparatus of claim 14, wherein the synthetic foam material distributes the pressure evenly on the ankle of the user.

16. The apparatus of claim 1, wherein the fabric covering, plurality of fabric straps, and pair of elongated fabric straps may be stitched together.

* * * * *